United States Patent [19]

Findl et al.

[11] 4,274,937

[45] Jun. 23, 1981

[54] APPARATUS FOR SENSING ELECTRICAL POTENTIALS

[75] Inventors: Eugene Findl, Amityville, N.Y.; Robert J. Kurtz, Cliffside Park, N.J.

[73] Assignee: Howmedica Inc., New York, N.Y.

[21] Appl. No.: 64,601

[22] Filed: Aug. 7, 1979

Related U.S. Application Data

[63] Continuation of Ser. No. 815,072, Jul. 12, 1977, abandoned.

[51] Int. Cl.³ .............................................. G01N 27/46
[52] U.S. Cl. ................................. 204/195 R; 204/1 T; 324/425; 324/453
[58] Field of Search ............ 204/195 R, 195 G, 195 F, 204/1 T

[56] References Cited

U.S. PATENT DOCUMENTS

| | | | |
|---|---|---|---|
| 2,382,735 | 8/1945 | Marks | 204/195 R |
| 2,414,411 | 1/1947 | Marks | 204/195 R |
| 2,517,382 | 8/1950 | Brinker et al. | 204/195 R |
| 2,651,612 | 9/1953 | Haller | 204/195 R |
| 2,768,135 | 10/1956 | Adelson | 204/195 F |
| 2,870,078 | 1/1959 | Hood | 204/195 R |
| 3,151,052 | 9/1964 | Arthur et al. | 204/195 F |
| 3,208,919 | 9/1965 | Sennett et al. | 204/195 R |
| 3,216,915 | 11/1965 | Arthur et al. | 204/195 G |
| 3,242,729 | 3/1966 | Keller | 204/195 R |
| 3,556,950 | 1/1971 | Dahms | 204/195 R |
| 3,709,796 | 1/1973 | King et al. | 204/195 R |
| 3,725,236 | 4/1973 | Johnson | 204/195 R |
| 3,839,162 | 10/1974 | Ammer | 204/195 G |
| 3,925,169 | 12/1975 | Baimbridge et al. | 204/195 F |
| 4,090,924 | 5/1978 | Bon | 204/195 R |

OTHER PUBLICATIONS

"Treatise on Analytical Chemistry", edited by Kolthoff and Elving, Part I, vol. 4, chapter 42, pp. 2127-2129.

*Primary Examiner*—T. Tung
*Attorney, Agent, or Firm*—Larson, Taylor and Hinds

[57] ABSTRACT

A sensor and method are disclosed for measuring electrokinetic effects across a double layer formed at the boundary between a solid wall and an ionic liquid flowing through a channel. In one embodiment, a passive electrode is located in a cavity forming a tee section with the channel through an orifice of approximately the same size as the channel. A passive second electrode in electrical communication with one side of the double layer is placed on the other side of a porous plug which is located in a second cavity directly opposite the orifice and which is flush with the channel walls. The double layer being investigated is formed on the flush portion of the porous plug. Thus both electrodes are out of the flowing liquid. An electrokinetic potential, labeled the K-effect potential, was measured by the two electrodes. In one use of the sensor, monitoring this potential, the chemical composition of the liquid can be maintained so as to keep a desired surface charge on suspended minerals which are being processed.

13 Claims, 7 Drawing Figures

APPARATUS FOR SENSING ELECTRICAL POTENTIALS

This is a continuation of application Ser. No. 815,072 filed July 12, 1977 now abondoned.

FIELD OF THE INVENTION

The present invention relates to the sensing and measurement of electrical potentials formed at the boundary between a double-layer forming fluid and a solid. More paticualrly, in one preferred embodiment, the present invention relates to a method and apparatus for sensing the change in electrical potential across a double layer formed at the surface of a phase change where the phase change can be that from a solid to a flowing ionic fluid. The present invention also relates to the use of such a sensor.

BACKGROUND OF THE INVENTION

According to the present electrokinetic theory, all electrokinetic phenomenon (e.g., streaming potential, electrophoresis, sedimentation potentials, and electroosmosis) are interrelated phenomenon and are based upon the fundamental electrochemical concept of the "double layer". The double layer concept was first described by Helmholtz in the last half of the nineteenth century and has been modified by many others since. In essence, an electrical double layer surrounds any surface in contact with a liquid and consists generally of an immobile layer of ions next to the surface and a mobile layer of ions electrostatically in equilibrium with the ions in the immobile layer. The Encyclopedia of Electrochemistry edited by Hampell (Reinhold Publishing Corp. 1964) identtified the double layer as follows.

"At any phase boundary there is always some redistribution of electrical charge because of the inhomogeneous field. This may be represented as two parallel sheets of charge of opposite sign known as a double layer. This name is retained even if the structure is more complex."

Clarles Reilley in his article entitled, "Fundamentals of Electrode Processes", *Treatise on Analytical Chemistry*, edited by Kolthoff and Elving (John Wiley and Sons, Inc. 1963), Part I, Volume 4, Chapter 42, at page 2127–2129, discusses in greater detail the electrical double layer. In particular, the double layer is analogized to the assemblage of a plurality of charged layers at the liquid-solid interface. Unfortunately, there is only a modicum amount of literature which discusses the electrokinetic effects at the double layer. Nevertheless, the principal difficulty of analyzing the double layer is well documented. See e.g., Bockris and Reddy, "Modern Electrochemistry", page 644, Volume 2 (Plenum Press 1974). Basically, the problem is that the introduction of an electrode into the liquid electrolyte sets up a second double layer. Thus, what is measured is the potential difference across two double layers in series and not just the double layer of interest.

The electrokinetic effects caused by changes in the double layer, if these effects could be accurately measured, have numerous practical applications. One application is in the mineral processing technology and particularly in the processing of low grade ores and ultrafine mineral particulates. Mineral processing involves many unit operations dealing with dispersions of a solid in a liquid where the dispersions range from course particles mixed with water to microscopic particles of colloidal size in a variety of liquid media. Separation of the desired mineral can be done by at least three general processes: sedimentation (e.g., decantation, flocculation, centrifugation, clarification, thickening, froth floatation, and electroflotation), filtration, (e.g., ultrafiltration, microfiltration, and expression) and electrical separation (electrophoresis, electrodialysis, electrodecantation, and electrochromatography, for example).

Each of the above processes involves a different primary mechanism for separation whereby sedimentation is a gravitational phenomenon, filtration is a pressure phenomenon, and electrical separation is an electrical phenomenon. However, each of the processes has the common factor that effects the degree of separation achieved, namely the surface charge of the particles.

Particle surface charge is generally assumed to be due to the establishment of a so-called ionic double layer on the surface of the particle. This double layer is believed to consist of ions and liquid molecules bound to the surface of the solid and counter ions, in the liquid near the surface, electrostatically attached to the bound ions. In essence, a solid particle immersed in a liquid, establishes a charge separation between itself and the bulk of the liquid. This charge separation in turn establishes a potential gradient and by physical and chemical manipulation of this potential gradient, it is possible to significantly improve the efficiency of the aforementioned processes. Consequently, in order to achieve maximum efficiency of the processes, it is important to be able to continuously measure the effects of the double layer potential (it being physically impossible to measure the double layer potential per se, as discussed above).

Unfortunately, all of the known conventional methods of measuring the effects of the double layer potential can be done only in a batch mode and not continuously. Some of the prior art electrokinetic techniques for measuring the effects of the double layer potential involve investigating streaming potential, electrophoretic mobility, and sedimentation potential. But there is no presently known way of investigating these effects under factory conditions on a continuous basis.

Present systems used to monitor the double layer effects and to maintain the surface of the particular mineral at the desired charge utilize pH and conductivity sensors. Such sensors however, do not measure surface charge but rather, based on prior experience and laboratory tests, the desired surface charge can be maintained by adjusting the pH and/or the conductivity of the dispersion. As a result, such a method does not provide real time information on the magnitude and polarity and the surface charge. In addition, in many of the aforementioned mineral processing operations, control of the surface charge of the dispersion cannot be done on a scientific basis.

Conventional sensors which can be used on a real time basis are effectively limited to pH sensors and conductivity sensors. Many of these sensors can be used to sample either the entire dispersion as it is being flowed through the processes or a sample of the dispersion. Typical conductivity cells. Are disclosed in the U.S. patents to Hood U.S. Pat. No. 2,870,078; to Adelson U.S. Pat. No. 2,768,135; and to Marks, U.S. Pat. No. 2,382,735. Although these references disclose conductivity cells that are useable in monitoring some of the above processes, they do not provide direct information about the double layer or about the surface charge.

SUMMARY OF THE INVENTION

The scientific basis of the present invention resides in the discovery by the present inventors of a new electrokinetic phenomenon detected at the double layer. As mentioned above, an ionic liquid in contact with a solid surface develops a double layer at the surface. This double layer has a capacitance and there is a potential difference across the double layer, although neither are measurable. However, if the liquid is flowed over the solid surface, the potential across the double layer changes. This change in potential, denoted the K-effect potential, can be measured. It has been found that the K-effect potential is directly proportional to the streaming potential and the double layer capacitance and is proportional to the log of the change in the concentration of the diffuse portion of the double layer. It is also believed that the K-effect potential equals the change in zeta potential from the zero flow to the flow conditions, where the zeta potential is usually defined in the literature as the potential difference between the immobile portion of the double layer and the bulk fluid.

If the double layer potential were plotted as a function of distance across the double layer at both zero flow and flow conditions, the resulting graph is believed to have the shape of two spaced apart, concave curves. If a zero potential is defined as the absolute potential in the bulk of the fluid, then the zeta potential for the no flow condition would be the point on the curve at the boundary between the immobile layer and the mobile layer of the double layer. This point is believed to shift vertically for the flow condition and this change in zeta potential equals the K-effect potential. It follows that the distance to the zero potential point is the spacing between the analogical double layer capacitance plates and the shift in this distance as a result of flow is the K-effect length. It is theorized that the shift in length occurs as a result of flow causing the double layer to extend out into the bulk of the fluid.

A purpose of the present invention is to provide a method of and a sensor for measuring the K-effect potential on a real time basis. Such a method and sensor could be used, for example, to sense the surface charge effects on mineral particles suspended in an ionic liquid. The present invention can be used in situ on a continuous basis to monitor the surface charge effects and the other double layer potential effects in mineral ore processing. The present invention also provides a means for generating control signals to change, modify or correct the liquid carrier used in mineral ore processing. For example, the present sensor can provide continuous surface charge information in real time to a microprocessor run controller.

This real time, accurate, reproducible surface charge information permits industrial ore beneficiation and handling processes to be operated with greater energy efficiency, better product quality control, less wastage of surface modifying reagents and higher throughput.

A sensor according to the present invention requires little maintenance, is capable of use by non-technically trained, non-skilled personnel. It can be inexpensively made, easily cleaned and maintained, and easily repaired. By charging only one component, the present sensor can be used with most of the minerals being processed and consequently is highly adaptable for a large variety of uses. The present sensor is also of very rugged construction, is damage resistant, is lightweight and is readily portable.

A sensor for attaining these and other advantages and objectives of the present invention comprises a solid wall along which a double-layer forming fluid can flow, whereby a double layer having an immobile layer in contact with the solid is formed at the boundary between the bulk of the fluid and the solid wall. A first, passive electrode is in electrical communication with the bulk of the fluid on one side of the double layer and a second passive electrode is in electrical communication with the immobile layer of the fluid along the wall on the other side of the double layer.

A method according to the present invention for monitoring the electrical properties of an ionic fluid flowing along a solid interface whereby a double layer is formed between the interface and the bulk of the fluid comprises the placing of a first passive electrode in electrical communication with the bulk of the fluid on one side of the double layer and placing a second passive electrode in electrical communication with the solid interface on the other side of the double layer. The changing electrical potential resulting from the fluid flowing along the interface and developed between the first and second electrodes is then detected. In one specific embodiment of the present invention which is used for sensing the surface charge of solid particles suspended in an ionic liquid, part of the solid interface is porous to ionic transport across the double layer formed thereon and is comprised of substantially the same chemical composition as that of the suspended solid particles. The second electrode is placed on the side of the interface which is out of physical contact with the flowing liquid.

Other details, features and objects of the present invention will be set forth in, or apparent from, the accompanying drawings and the detailed description of presently preferred embodiments found hereinbelow.

DETAILED DESCRIPTION OF THE PRESENTLY PREFERRED EMBODIMENTS

Figure 1:
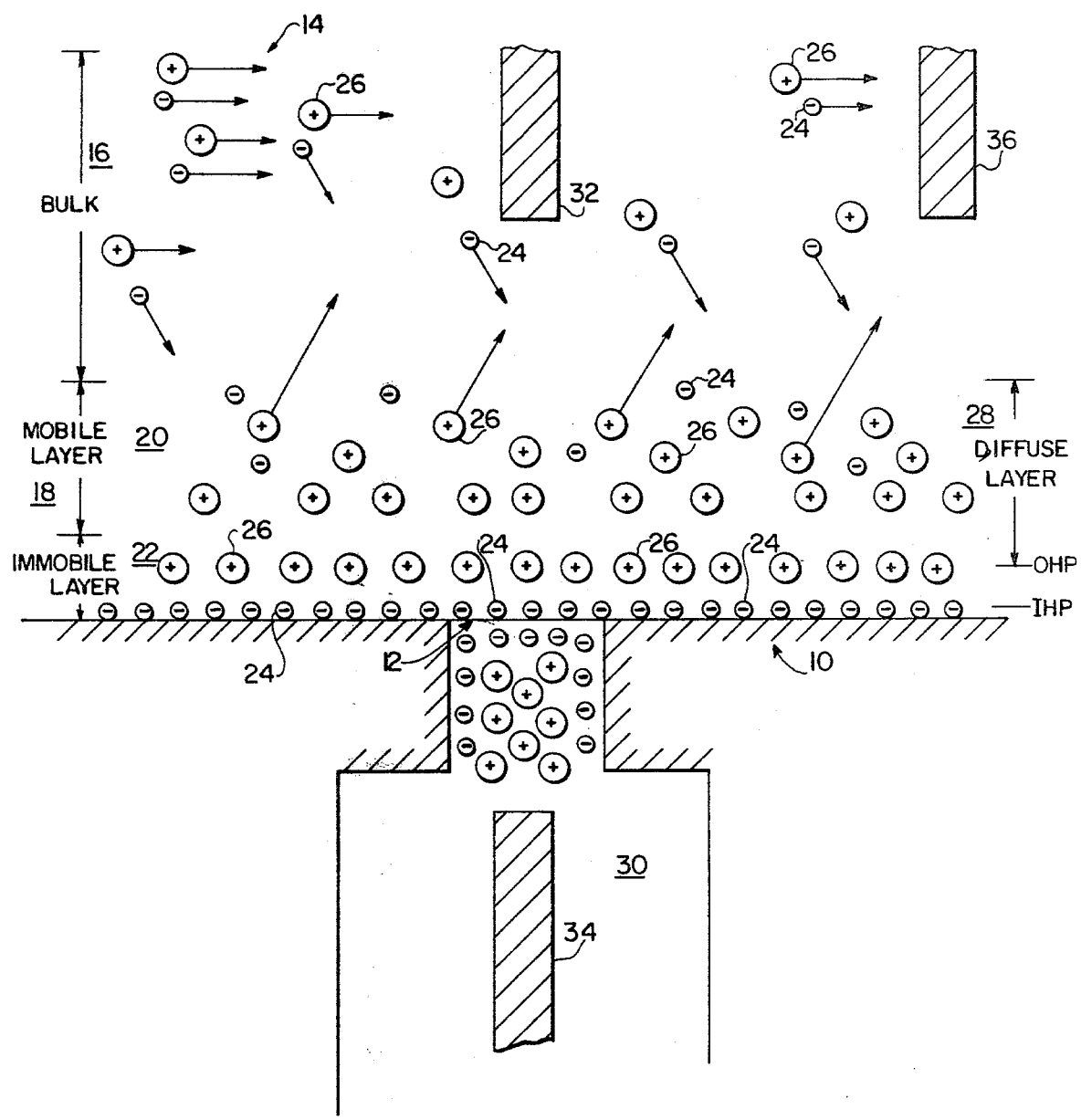
FIG. 1 is a diagrammatic representation of a model of the double layer mechanism schematically showing the present invention for detecting the electrokinetic potentials associated with the double layer.

Reference is now made to the several figures wherein like numerals designate like elements throughout the several views. With reference to FIG. 1, a model of the double layer is depicted. A solid wall 10 having a porous portion 12 forms an interface with a flowing fluid, such as an ionic liquid 14. The ionic liquid 14 comprises a bulk portion 16 and a double layer portion 18 which in turn is comprised of a mobile layer 20 and an immobile layer 22. Immobile layer 22, in turn, is theoretically comprised of an inner Helmholtz plane, IHP, comprised of, for example, a high concentration of anions 24 next to wall 10 and an outer Helmholtz plane, OHP, which contains mainly solvated cations 26 (e.g., cations surrounded by water of hydration molecules). Beyond the outer Helmholtz layer extends a diffuse layer 28 with a net charge as a result of excess cations residing therein because fewer cations can reside in the outer Helmholtz layer as a result of the lager size of the cation. From a concentration standpoint, there is thus an excess of cations over anions in the diffuse portion of double layer 18.

According to the present theory, when ions in bulk portion 16 of liquid 14 are caused to flow, there is an interchange of ions with the mobile portion of double layer 18. This interchange results in a decrease in the concentration of cations in the mobile layer 20 and a slight increase, though normally negligible, in cation concentration in the bulk portion 16. Since anion concentration in mobile layer 20 is lower than that of bulk portion 16 under no flow conditions, the flowing of bulk portion 16 causes an influx of anions to diffuse layer 28. It is the increase in anion concentration and decrease in cation concentration of diffuse layer 28 of double layer 18 that gives rise to the K-effect potential. Furthermore, it is believed under the present theory that the K-effect potential establishes streaming potentials.

The establishment of streaming potentials can be illustrated by an electrical analog of a ladder resistance network. The bottom plurality of resistances represent resistive components of unit length of a solid wall. The top plurality of resistances represent the bulk fluid electrolytic resistance. A plurality of interconnecting resistances between the top and bottom resistances represent the resistance of the double layer. Under flow conditions, a battery-like potential exists between the junction of the wall and double layer resistances and the diagonal junction in the direction of fluid flow between the bulk and double layer resistances.

Turning again to FIG. 1, porous wall portion 12 separates a fluid containing cavity 30 and permits ionic transport across double layer 18 into cavity 30. In this embodiment, porous wall portion 12 can merely consist of a plurality of very small orifices through wall 10. A first K-effect electrode 32 is schematically shown in electrical communication with the liquid bulk portion 16 on one side of double layer 18. On the other side of double layer 18 is a second electrode 34 located out of the flowing stream in cavity 30. Second electrode 34 is in electrical communication with immobile layer 22 of liquid 14 along the wall on the other side of double layer 18 as a result of the ionic porosity of porous wall portion 12. A third electrode 36 is illustratively, schematically shown downstream of first electrode 32. The potential developed between first electrode 32 and third electrode 36 is conventionally referred to as the streaming potential. The potential developed by the flowing liquid between first electrode 32 and second electrode 34 is the K-effect potential.

In a presently preferred embodiment, the three electrodes are silver/silver chloride wire electrodes. Each of the electrodes are as similar as possible to each other in composition, length, diameter, shape, and mounting means. It is preferable if both first and second electrodes 32 and 34 are out of physical contact with the flowing liquid and are located at the same point along wall 10. It is noted that a double layer would also be formed at the surfaces of electrodes 32, 34 and 36. However, for the sake of simplicity, this further double layer has been omitted. In addition, the cation hydration sheet around cations 26 has not been illustrated.

Figure 2:
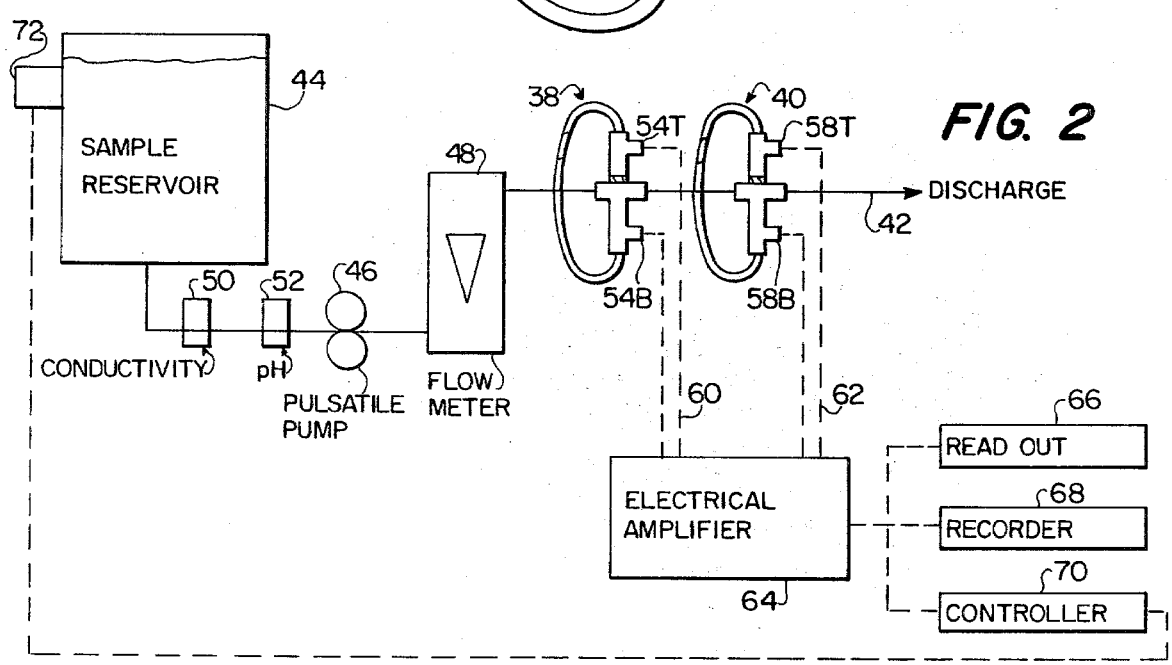
FIG. 2 is a schematic flow chart of a sensing system using a plurality of serially connected sensors according to the present invention.

In FIG. 2 two substantially identical K-effect sensors 38 and 40 are respectively, mutually located upstream and downstream in an ionic liquid sample line 42. A sample reservoir 44 can be used to hold a supply of the sample liquid. Alternatively, the sample can be drawn directly from an ongoing process and either returned to the process or discharged, or can include the entire liquid flow in the process.

A pump 46 is used to provide pulsatile flc through sample line 42. Alternatively, a centrifugal pump could be used to provide a continuous, and hence DC type of flow. In certain applications, it is preferable to use a pulsatile type of fluid flow so that background noise and other signal errors or undesirable signals will be cancelled out. Various measuring instruments can also be located in sample line 42 such as a flow meter 48, a conductivity cell 50 and a pH cell 52.

The upstream sensor 38 has a top electrode 54T on one side of a porous plug 56 (see FIG. 3) and a bottom electrode 54B in direct electrical communication with the bulk portion of the fluid flow. Similarly, downstream sensor 40 has a top electrode 58T and a bottom electrode 58B. The two pairs of electrodes are respectively coupled through wires 60 and 62 to an electrical amplifier 64. The signal from amplifier 64 can go to an immediate readout device 66, a chart recorder 68, and a controller 70. Controller 70 can be a microprocessor which monitors not only the K-effect potentials sensed by electrodes 54T and 54B, and by electrodes 58T and 58B, but also the streaming potential measured by electrode pairs 54T and 58T and 54B and 58B, the pH measured by pH cell 52, and the conductivity measured by conductivity cell 50. Controller 70 can be electrically connected to chemical addition means, schematically shown at 72, so that the desired surface charge can be maintained on the suspended particles in the liquid.

Figure 3:
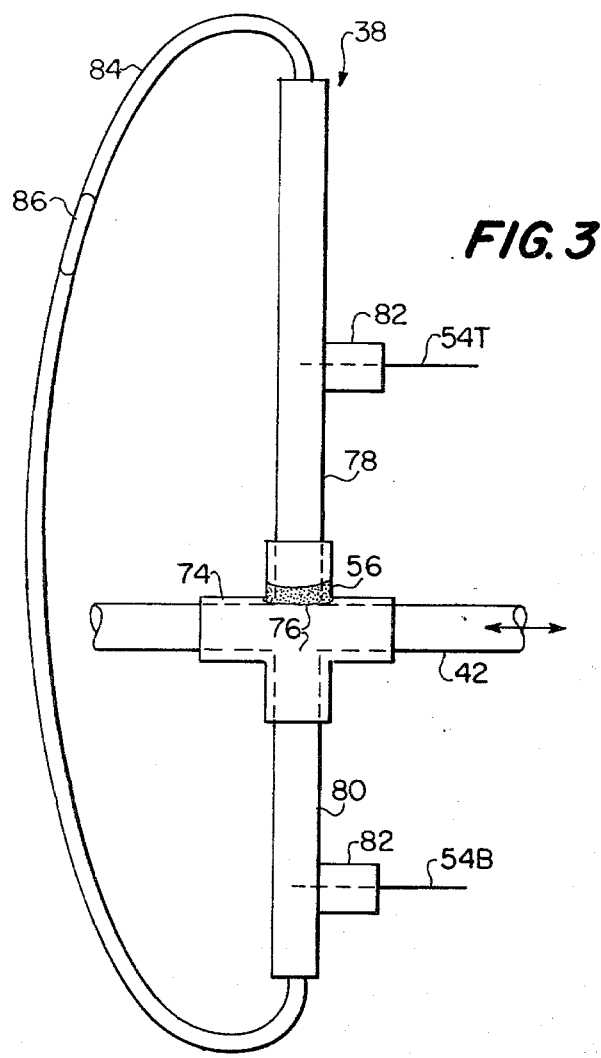
FIG. 3 is an enlarged elevational view of one embodiment of a sensor according to the present invention.

Sensor 38 is depicted in greater detail in FIG. 3. Because sensor 38 is similar to sensor 40, only the former will be described. Sensor 38 comprises a tee connection 74 through which sample line 42 is extended in the horizontal direction. Two orifices 76 directly opposite each other in sample line 42 permit communication of the liquid flowing through sample line 42 with tee connection 74 in upper and lower vertical directions. An upper tubing 78 and a lower tubing 80 are fitted into the respective arms of tee connection 74. Electrodes 54T and 54B are inserted through fittings 82 and are in physical contact with the liquid located in upper and lower tubings 78 and 80, respectively. As mentioned above, porous plug 56 is inserted in the upper arm of tee connection 74 and prevents direct fluid communication between sample line 42 and upper tubing 78, but permits ionic transport therethrough. The bottom surface of porous plug 56 extends through top orifice 76 in sample line 42 and is preferably flush with the inner wall of sample line 42. A capillary tubing 84 connects the distal ends of upper and lower tubings 78 and 80 and has a means therein, such as an air bubble 86, intermediate the ends of tubing 84 for preventing fluid and electrical communication therebetween, but for permitting equalization of pressure on either side of porous plug 56.

Thus, electrode 54B is located in a well formed by lower tubing 80 and fitting 82. The well is in fluid communication with the liquid flow path formed by sample line 42 and the horizontal arms of connection 74 at the same position in the flow path as porous plug 56, namely directly opposite porous plug 56. However, electrode 54B while in direct fluid communication with a fluid when flowing through the flow path is located out of the path of the flowing liquid.

Upper and lower tubings 78 and 80 and tee connection 74 are preferably made of a plastic such as "Lexan". Electrodes 54T and 54B are mounted in their respective tubing 78 and 80 in nylon compression tube fittings. Capillary tubing 84 should be made of a non-conductive material such as polyethylene and in one example had an inner diameter of 1.5 millimeters. In this embodiment, capillary tubing 84 was approximately 25 centimeters long. Porous plug 56 can be made from any substance that can be made porous, that is contains micropores which are defined as having a diameter of less than 0.001 inch. There are numerous conventional ways for making a porous structure of almost any material. Some porous materials can include filter cakes, foams, emulsions, and sintered metals.

Figure 7:
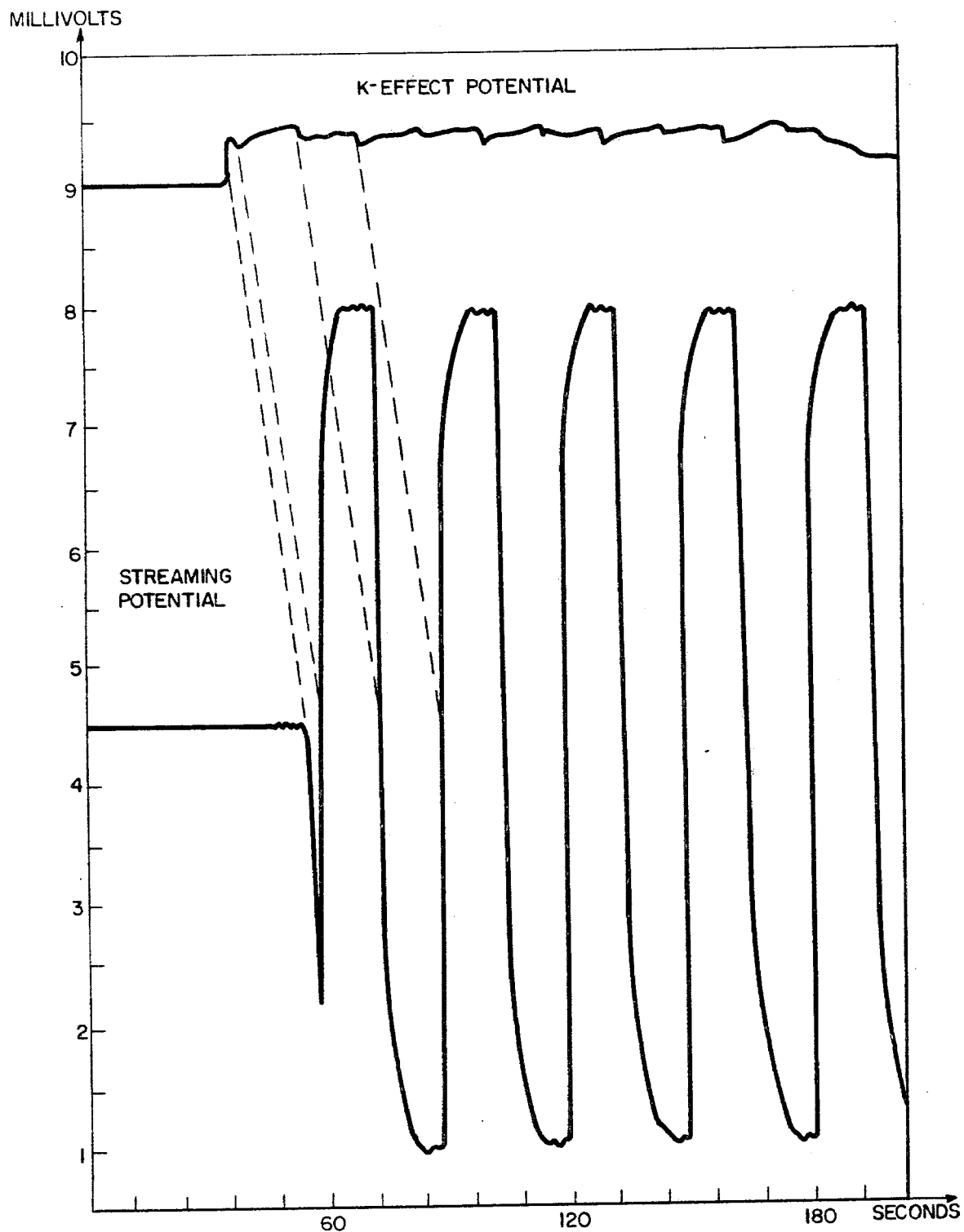
FIG. 7 is a chart of a measured K-effect potential showing its timed relationship to flow reversals and the measured streaming potential.

The results of one particular test run using a plurality of sensors in a configuration such as shown in FIG. 2 wherein the electrodes were spaced 10 centimeters apart is depicted in FIG. 7. The K-effect potential is shown on the upper trace and is mechanically displaced on the time axis from the simultaneously measured streaming potential depicted in the lower trace. Dash lines interconnect simultaneous time points. The zero flow situation is shown as the initial starting line. Each major division of the chart in the vertical direction represents a potential of 10 millivolts and chart speed was 5 centimeters per minute. Flow direction reversals are indicated by streaming potential reversals and dips in the K-effect potentials. The measurement depicted in FIG. 7 was made using a dual pen strip chart recorder with voltage followers having greater than $10^{10}$ ohm input impedance used to minimize electrode currents.

The electrolyte resistivity for the test the results of which are depicted in FIG. 7 was $2.8 \times 10^5$ omh cm. The temperature was 22° centrigrade and the pH was 6.8. The particular plug was made of porous acrylic material and flow rates of approximately 160 milliliters per minute were used.

It is apparent from FIG. 7 that the K-effect potential is independent of flow direction and is dependent upon flow rate. On the other hand, streaming potential is dependent on flow rate and direction as clearly shown in FIG. 7. Other tests with various electrolyte resistivities and with different electrolytes demonstrated that the K-effect potential is dependent upon the physical characteristics of the electrolyte and the suface charge of the porous plug. For example, aluminum nitrate reverses the polarity of both the K-effect potential and the streaming potential.

Figure 5:
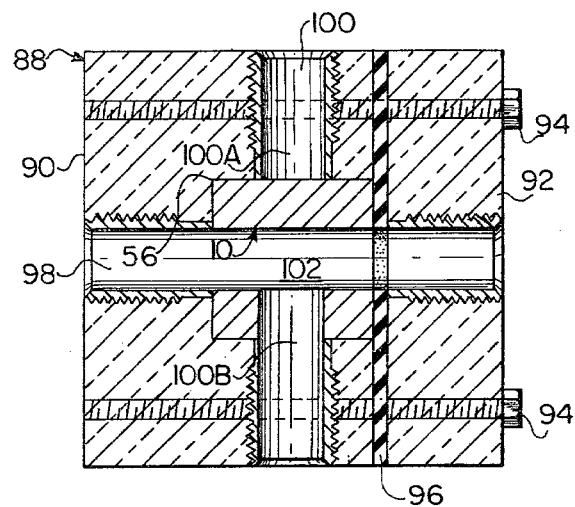
FIG. 5 is a cross-sectional view taken along line 5—5 of FIG. 4.
Figure 4:
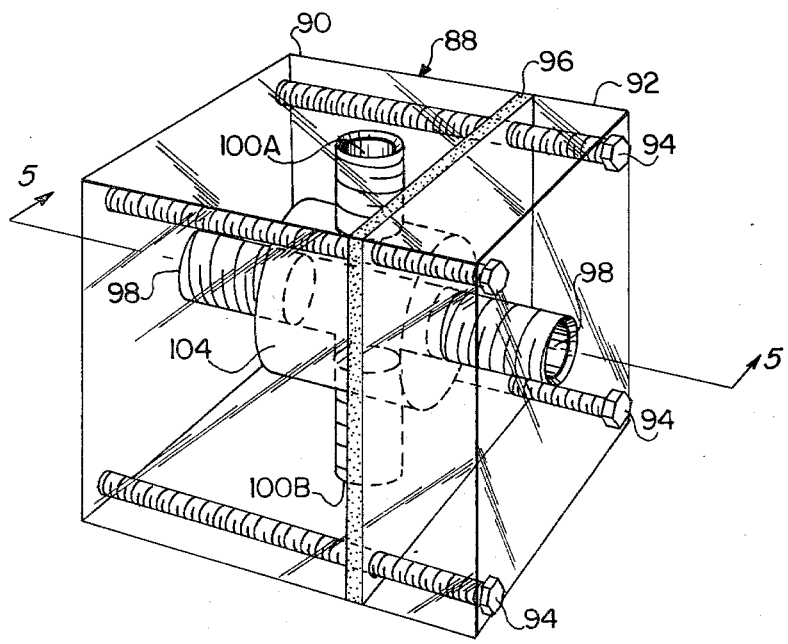
FIG. 4 is a perspective view of part of a sensor according to a second embodiment of the present invention.

A second embodiment of a housing 88 of another sensor according to the present invention is depicted in FIGS. 4 and 5. Housing 88 is comprised of a main body portion 90 and a cap portion 92 rigidly held together with means such as screws 94. A rubber gasket 96 is used to provide a fluid tight fit between body portion 90 and cap portion 92. Two bores, a horizontal main bore 98 and a vertical side bore 100 are drilled completely through housing 88 and intersect approximately at the midpoints thereof at a junction 102. If desired, the ends of the bores can be threaded for receiving connecting tubing. For example, main bore or channel 98 is connected at each end to sample line 42 (FIG. 2), the upper part of side bore or channel 100 A is connected to an upper tubing in which top electrode 54T is inserted, and the lower portion of side bore or channel 100B is connected to a lower tubing in which bottom electrode 54B is inserted. It is preferable that main channel 98 and side channel 100 are the same size and have straight and smooth inner walls. Exemplary dimensions of housing 88 are a 1½ inch cube with ¼ inch bores being drilled therethrough. Housing 88 can be made from an insulating material such as "Nylon" and gasket 96 can be made from butyl rubber. In any event, gasket 96 should be made of insulative material.

That part of main channel 98 in main body portion 90 which abuts cap portion 92 is enlarged to form a cylindrical chamber 104. Chamber 104 extends inwardly past junction 102 and is for receiving a cylindrical type of porous plug 56. Plug 56 would have a horizontal channel drilled completely therethrough for coaxial abutment with main bore 98. In addition, a lower bore is drilled through plug 56 for coaxial abutment with bottom side channel 100B. In this manner, the top portion of the inner plug wall defining the bore therethrough becomes the solid wall 10 of FIG. 1 along which a double layer is formed. The thickness of the upper wall of plug 56 can have dimensions from a few angstroms to 1/16 of an inch. It has been found that this thickness is overly critical, the only critical part being that ionic transport can readily take place through plug 56. Similarly, the dimensions of channels 98 and 100 is not critical, but it is preferable that they be large enough so that there are no capillary effects.

The advantages of using a sensor with a housing as depicted in FIGS. 4 and 5 are fairly obvious. For example, a plurality of porous plugs 56 can be readily changed simply by loosening screws 94, removing cap portion 92, and inserting a plug 56 into chamber 104. In addition, housing 88 can be very inexpensively manufactured, has an indefinite shelf life, is rugged and not easily damaged, and can be easily connected into a system.

It is noted that although the sensor according to the present invention may appear to be similar to conventional conductivity cells, the two are completely different instruments which operate on different principles. The conductivity cell has active electrodes which are used to provide a known EMF to the liquid, thereby generating a current in the liquid. On the other hand, the present invention has passive electrodes which merely monitor the potentials sensed across a double layer. In fact, in one embodiment of the invention, high impedance voltage followers were used to minimize electrode currents. There is also no impressed voltage on electrodes of the present sensor and for this reason, they are denoted "passive electrodes". In addition, in another preferred embodiment the electrodes are directly coupled to the ionic fluid being monitored and there is no intermediate electrolyte. Some of the conductivity cells, such as those disclosed in the previously cited references, use an electrolyte in contact with a salt bridge.

Although sensors have been disclosed in presently preferred embodiments, certain modifications can be made to the electrodes within the scope and spirit of the invention. Thus, for example, capillary tubing 84 may not be necessary on some electrodes and in those cases, upper and lower tubing 78 and 80 would have their ends sealed and upper tubing 78 would be filled with a liquid, preferably the same liquid as that flowing through sample line 42.

Figure 6:
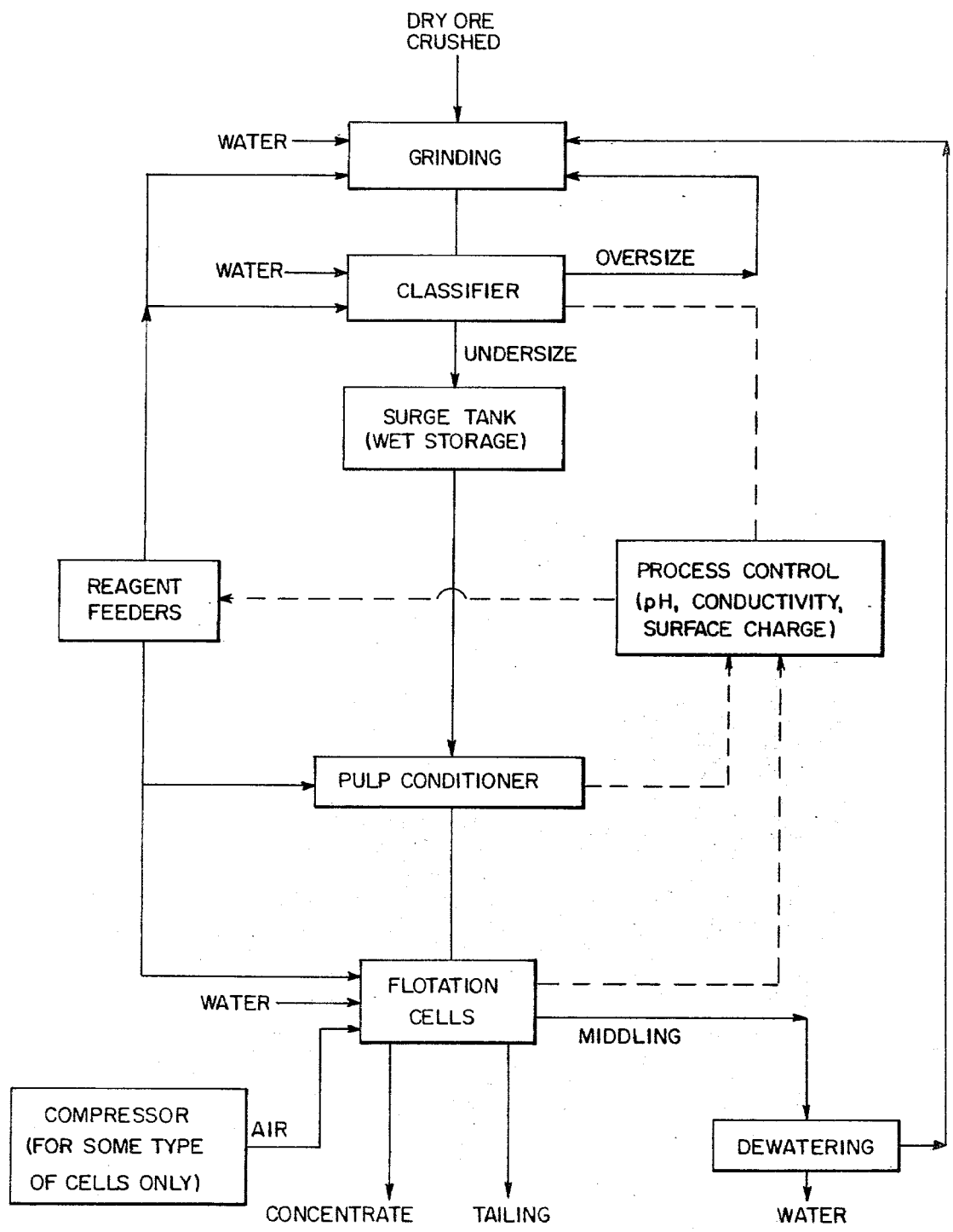
FIG. 6 is a schematic flow chart of a typical floatation mineral separation process in which the present invention can be used.

A sensor as described hereinabove according the the present invention can be most conveniently used in a flotation process for recovery of valuable minerals from low yield ores. The flow chart of a froth flotation process is depicted in FIG. 6 and is used to separate one kind of particulate solid from another through their selective attachment to air bubbles in an aqueous suspension. The particle attached to the air bubble floats to the top of a liquid bath, leaving the other constituents behind. The process is quite conventional and therefore will not be described in greater detail.

It is noted that there are a number of interacting factors that can be used to control or modify the surface property of ores. Among these factors are the use of surface active agents, the presence of inorganic ions, and the pH of the fluid. Usually, anionic surfactants are effective for the flotation of goethite below pH 6.7. Above this pH value, catonic surfactants are required for flotation. The explanation for this phenomenon appears to be that at pH equal to 6.7, the zeta potential is zero. Above pH of 6.7, the zeta potential is negative which means that the particle being floated has a negative surface charge. Below a pH of 6.7, the opposite is true. Consequently, by monitoring the surface charge, the critical operational area can be maintained. A sensor and a method according to the present invention can easily be used to monitor on a real time, continuous basis the K-effect potential which, as mentioned above, is related to the zeta potential. Different mineral processing operations require different surface charges. For optimal separation via flotation, it is generally desired to have the surface of the desired mineral charged and hydrophobic so that the mineral particle will readily attach itself to an air bubble. The foregoing, of course, is only an exemplary use of a plurality of uses of the present invention.

Although the invention has been described in detail with respect to exemplary embodiments, thereof, it will be understood by those of ordinary skill in the art that variations and modifications may be effected within in the scope and spirit of the invention.

We claim:

1. Apparatus for sensing the voltage changes in the electrical potentials at the boundary formed between a flowing fluid and a solid whereby a double layer having an immobile layer in contact with the solid is formed between the boundary and the bulk of the flowing fluid, the apparatus including a sensor comprising:
    a solid wall having a porous portion therein that is porous to ionic flow, but impervious to direct fluid communication therethrough;
    inlet means for introducing a flowing fluid to one end portion of said solid wall;
    means for directing the introduced fluid to flow along said wall;
    outlet means for conducting the directed flowing fluid away from the other end portion of said solid wall, said inlet means, said wall, and said outlet means providing a flow path completely through said sensor;
    a first passive electrode;
    a well located at the same position in said flow path as said porous portion, said well being to fluid communication with said flow path, but having no flowing therethrough;
    first means for mounting said first passive electrode in said well, and thus on one side of said porous portion and spaced from said wall out of said flow path and thus adapted to be in direct electrical contact with the bulk of the fluid on one side of the double layer formed at said porous portion when the fluid is flowing through said flow path along said solid wall;
    a second passive electrode of substantially the same composition as said first electrode; and
    second means for mounting said second passive electrode on the other side of said porous portion in electrical contact with a fluid when flowing through said flow path, said second electrode thereby being mounted out of physical and direct electrical contact with the fluid when flowing through said flow path and said second electrode thereby being mounted in electrical contact through said porous portion with the immobile layer of the fluid when flowing along said one side of said porous portion and thus on the other side of a formed double layer.

2. A sensor for sensing changes in the electrical potentials developed across a double layer formed by a flowing ionic fluid between the bulk of the flowing fluid and a boundary having a phase different from the fluid, the sensor comprising:
    a conduit having a wall defining a flow path for a fluid, a portion of said conduit wall including a porous member that is porous to ionic transport and that has a phase that is different from the phase of the fluid when flowing in said flow path, said conduit having a well located at the same position in said flow path as said porous member, said well being in fluid communication with said flow path, but having no flow therethrough;
    a first passive electrode mounted in said well and thus spaced from one side of said porous member out of the fluid flow path, but adapted to be in fluid and direct electrical communication with the bulk portion of a fluid when flowing through said flow path and hence adapted to be in direct electrical communication with one side of a double layer which is formed by the flowing fluid at said porous member; and
    a second passive electrode of substantially the same composition as said first electrode mounted on the other side of said porous member outside said fluid flow path, but in electrical contact therewith through said porous member, and hence adapted to be out of physical contact with a fluid when flowing through said fluid flow path, but in electrical communication with a fluid when flowing through said flow path on the other side of a double layer formed at said porous member.

3. A sensor as claimed in claim 2 wherein said conduit portion comprises a solid and said conduit portion partly defines said flow path.

4. A sensor as claimed in claim 3 wherein said conduit comprises a solid wall that defines a flow path therethrough and said sensor is for sensing electrical potentials across a double layer formed when an ionic liquid flows through said conduit along said solid wall, the double layer being formed between said wall and the bulk of the flowing liquid.

5. A sensor as claimed in claim 2 wherein said sensor is comprised of a conduit completely therethrough, said conduit having solid walls;

and wherein said well comprises a first side channel in fluid communication with said conduit at a first junction, said first junction having an opening into said first side channel of a size such that the bulk of a fluid flowing in the conduit is in fluid communication with said first side channel.

6. A sensor as claimed in claim 5 wherein said sensor is for use with an ionic liquid and said sensor further includes:

a second side channel in fluid communication with said conduit at a second junction located at substantially the same location along said conduit as said first junction; and wherein said porous member is a solid and is porous to ionic flow from an ionic liquid when flowing therealong across a double layer formed thereat, said porous member being located at said second juncture and for preventing the bulk portion of a liquid when flowing through said flow path from entering said second side channel, the double layer being formed along one side of said porous member; and wherein said second side channel contains a conductive liquid and said second electrode is mounted in said second side channel in said liquid in electrical communication with a liquid in said flow path through said channel liquid and said porous member.

7. A sensor as claimed in claim 6 further including a non-conductive, hollow tubing connected at one end thereof to said first side channel and at the other end thereof to said second side channel and means intermediate said tubing ends for preventing fluid and electrical communication therebetween but for permitting equilization of pressure on either side of said porous solid member.

8. A sensor for sensing changes in the electrical potentials developed across a double layer formed by a flowing ionic liquid between a solid boundary substantially parallel to the flow and the bulk of the liquid, the sensor comprising:

a housing comprised of an electrically non-conductive body;

a first channel completely through said body for providing unobstructed flow of a liquid through said body;

a second channel in said body in communication with said first channel through a first aperture therein, said aperture having a size such that the bulk of a liquid when in said first channel is in fluid communication with said second channel;

a third channel in said body having a second aperture therein, said second aperture being located directly opposite said first aperture and said second and third channels substantially forming a cross with said first channel;

a porous solid member porous to ionic flow from an ionic liquid flowing through said first channel, said porous member being located in said second aperture, a first, liquid contacting side thereof being substantially flush with the walls of said first channel such that a double layer can be formed therealong;

a passive first electrode mounted in said second channel spaced from said first aperture and adapted to be out of direct contact with the moving part of a liquid when a liquid is flowing in said first channel, but in direct electrical contact with the bulk of the liquid; and a passive second electrode of substantially the same composition as said first electrode, said second electrode being mounted in said third channel on the other side of said porous solid member and adapted to be in electrical communication with a liquid when flowing in said first channel through said porous solid member.

9. The sensor as claimed in claim 8 wherein the diameter of said second channel, the diameter of said first aperture and the diameter of said first channel are substantially the same.

10. The sensor as claimed in claim 9 wherein said first and second channels are substantially cylindrical and the walls defining said first channel are substantially smooth.

11. Apparatus as claimed in claim 1 and further including comparing means for comparing the electrical potentials of said first and second electrodes and for producing an output based on the difference in said electrical potentials.

12. Apparatus for sensing changes in an electrical potential developed by a flowing ionic liquid, the apparatus including a sensor comprised of a housing having a conduit therein with a wall defining a flow path completely therethrough, a conduit inlet, a conduit outlet, a first orifice in said conduit wall, an internal well in fluid communication with said flow path through said first orifice, a second orifice in said conduit wall at the same location along said conduit as said first orifice, and an internal chamber connected to said flow path through said second orifice, said chamber for containing an ionic liquid when said sensor is being used;

a porous plug securely mounted in said second orifice such that one end thereof is substantially coplanar with said conduit wall, said plug being porous to ionic transport therethrough, but preventing any liquid flow through said second orifice;

a first passive electrode mounted in said well away from said flow path so as to be out of contact with the flowing portion of a liquid when flowing in said flow path but in direct electrical contact therewith; and a second passive electrode mounted in said chamber, said second electrode being of substantially the same composition as said first electrode and being in electrical contact with a fluid in the flow path only through the liquid in said chamber and through said porous plug.

13. Apparatus as claimed in claim 12 and further including comparing means for comparing the electrical potentials of said first and second electrodes and for producing an output based on the difference in said electrical potentials.

* * * * *